United States Patent [19]
Cook et al.

[11] Patent Number: 5,766,931
[45] Date of Patent: *Jun. 16, 1998

[54] COMPOSITION AND METHODS FOR DESTROYING HYDROGEN PEROXIDE

[75] Inventors: James N. Cook, Mission Viejo; John L. Worsley, Irvine, both of Calif.

[73] Assignee: Allergan, Waco, Tex.

[ * ] Notice: The term of this patent shall not extend beyond the expiration date of Pat. No. 5,362,647.

[21] Appl. No.: 773,425

[22] Filed: Dec. 27, 1996

Related U.S. Application Data

[62] Division of Ser. No. 515,756, Aug. 15, 1995, which is a division of Ser. No. 259,207, Jun. 13, 1994, Pat. No. 5,521,091, which is a division of Ser. No. 17,232, Feb. 12, 1993, Pat. No. 5,362,647.

[51] Int. Cl.⁶ ............................................ C12S 9/00
[52] U.S. Cl. .................. 435/264; 435/264; 435/192; 435/917; 424/468; 424/94.4; 422/30
[58] Field of Search .......................... 435/264, 192, 435/917; 424/406, 418, 616, 468, 94.4, 408; 252/106, 174.12; 422/30

[56] References Cited

U.S. PATENT DOCUMENTS

| | | |
|---|---|---|
| Re. 32,672 | 5/1988 | Huth et al. . |
| 2,635,069 | 4/1953 | Baker . |
| 3,123,539 | 3/1964 | Beers, Jr. . |
| 3,930,953 | 1/1976 | Stark . |
| 4,585,488 | 4/1986 | Giefer . |
| 4,588,586 | 5/1986 | Kessler et al. . |
| 4,775,424 | 10/1988 | Wisotzki et al. . |
| 4,826,658 | 5/1989 | Kay . |
| 4,959,212 | 9/1990 | Stancesco et al. . |
| 5,011,661 | 4/1991 | Schafer et al. . |
| 5,080,886 | 1/1992 | Mickle et al. . |
| 5,145,644 | 9/1992 | Park et al. . |
| 5,360,732 | 11/1994 | Berka et al. . |
| 5,360,901 | 11/1994 | Berka et al. . |
| 5,362,647 | 11/1994 | Cook ........................ 435/264 |
| 5,521,091 | 5/1996 | Cook ........................ 435/264 |
| 5,521,291 | 5/1996 | Cook . |

FOREIGN PATENT DOCUMENTS

| | | |
|---|---|---|
| WO9211041 | 7/1992 | WIPO . |
| WO9217571 | 10/1992 | WIPO . |
| WO9317721 | 2/1993 | WIPO . |

OTHER PUBLICATIONS

ATCC "Catalogue of Bacteria & Bacteria Phazes", 17th ed. Rockville, MD 1989 p. 130.

*Primary Examiner*—Carolyn Paden
*Attorney, Agent, or Firm*—Frank J. Uxa

[57] ABSTRACT

Compositions and methods for destroying hydrogen peroxide, for example, contact lens disinfecting amounts of hydrogen peroxide, are disclosed. The present invention utilizes non-mammalian-derived catalase, for example, catalase obtained as a result of the action of one or more microorganisms such as *Micrococcus luteus*, *Aspergillus niger* and mixtures thereof, to promote the destruction of hydrogen peroxide. Such non-mammalian-derived catalase has substantial advantages, e.g., enhanced stability, relative to bovine catalase, which is conventionally used in such contact lens-related applications.

14 Claims, No Drawings

5,766,931

COMPOSITION AND METHODS FOR DESTROYING HYDROGEN PEROXIDE

This is a division of application Ser. No. 08/515,756 Filed Aug. 15, 1995, which in turn is a division of application Ser. No. 08/259,207, Filed Jun. 13, 1994, now U.S. Pat. No. 5,521,091 which in turn is a division of application Ser. No. 08/017,232, Filed Feb. 12, 1993, now U.S. Pat. No. 5,362,647.

BACKGROUND OF THE INVENTION

This invention relates to destroying hydrogen peroxide, for example, hydrogen peroxide used in disinfecting lenses, such as contact lenses. In particular, the invention relates to compositions and methods useful to quickly and effectively destroy hydrogen peroxide and disinfect, and preferably clean, such lenses while reducing eye irritation caused by disinfecting the lenses.

Contact lenses should be periodically disinfected and cleaned by the user to prevent infection or other deleterious effects on ocular health which may be associated with contact lens wear. Currently, there are several different conventional systems and methods which enable the user to clean and disinfect his/her contact lenses between wearing times. These conventional cleaning and disinfection systems can be divided into "hot" and "cold" systems. Hot systems require the use of heat to disinfect the contact lenses, whereas cold systems use chemical disinfectants at ambient temperatures to disinfect the lenses.

Within the realm of cold disinfection systems are hydrogen peroxide disinfection systems. Disinfecting hydrogen peroxide solutions are effective to kill the bacteria and fungi which may contaminate contact lenses. However, residual hydrogen peroxide on a disinfected contact lens may cause irritation, burning or trauma to the eye unless this hydrogen peroxide is destroyed, i.e., decomposed, neutralized, inactivated or chemically reduced. Therefore, destruction of the residual hydrogen peroxide in the liquid medium containing the disinfected contact lens is needed to enable safe and comfortable wear of the disinfected contact lens. Liquid media (not including the hydrogen peroxide contained therein) used to disinfect contact lenses should be substantially isotonic, for example, to the human eye, and preferably ophthalmically acceptable so as to reduce the chances of problems caused by placing the disinfected lenses in the wearer's eyes.

Catalase, in particular bovine catalase, for example, catalase obtained from beef livers, has been effectively used to promote the destruction of residual hydrogen peroxide contact lens disinfectant. See, for example, Giefer U.S. Pat. No. 4,585,488. While bovine catalase is very useful in this contact lens-related, hydrogen peroxide destruction service, it would be advantageous to employ a still more active and/or stable agent to facilitate the destruction of hydrogen peroxide contact lens disinfectant.

Other catalases, that is catalases obtained from other than bovine sources, are known, for example, as agents useful in decomposing relatively low concentrations (in the parts-per million (ppm) range) of hydrogen peroxide in industrial waste waters. Baker U.S. Pat. No. 2,635,069 discloses catalase obtained from molds, such as *Penicillium chrysogenum, Penicillium notatum* and *Aspergillus niger* to decompose hydrogen peroxide under industrial conditions, such as in the manufacture of furs, foam rubbers, textiles, feathers, soaps and foods. Beers, Jr. U.S. Pat. No. 3,123,539 discloses catalase derived from bacterial sources, such as *Micrococcus lysodeikticus*, as being more active than catalase produced from other sources. This patent does not disclose any specific use for catalase. However, to the present inventors' knowledge, the prior art has not disclosed or suggested the use of any non-mammalian-derived catalase in contact lens disinfecting service.

There continues to be a need for a contact lens care system which rapidly and effectively disinfects, and preferably cleans, a contact lens so that the disinfected lens can be safely and comfortably worn.

SUMMARY OF THE INVENTION

New compositions and methods useful in disinfecting, and preferably cleaning, a lens, preferably a contact lens, and in destroying residual hydrogen peroxide disinfectant have been discovered. These compositions and methods take advantage of enhanced properties of non-mammalian derived catalases, for example, relative to bovine catalase. Not only are the presently useful non-mammalian-derived catalases, hereinafter referred to as NMDC's, often more active than bovine catalase in this service, but such NMDC's have been found to have enhanced stability relative to bovine catalase.

This enhanced stability facilitates commercial production and distribution of contact lens care products including such NMDC's. For example, NMDC's often have enhanced activity stability during manufacturing, such as during the production of tablets containing such NMDC's. Also, the enhanced stability of the NMDC's allows a longer effective product shelf life. Further, the present NMDC's are preferably more stable at elevated temperatures and/or over a broader pH range than is bovine catalase. This stability advantage allows one more latitude in choosing the conditions at which the contact lens is to be disinfected. In effect, such conditions can be chosen to assure rapid and effective lens disinfection with less concern that such conditions will interfere with the action of the catalase. Moreover, the presently useful NMDC's are preferably less susceptible to deactivation in high concentrations of hydrogen peroxide (such as that used in contact lens disinfecting) than is bovine catalase. This feature can result in more rapid destruction of hydrogen peroxide relative to the same initial active amount of bovine catalase or in comparable hydrogen peroxide destruction results with amounts of NMDC's which are reduced relative to the amount of bovine catalase needed to achieve such results.

In one broad embodiment, the present invention involves methods for destroying hydrogen peroxide. Such methods comprise contacting a contact lens with a liquid medium containing hydrogen peroxide in the presence of NMDC in an amount effective to promote the destruction of substantially all the hydrogen peroxide in the liquid medium. The NMDC employed in the present methods has preferably been obtained as a result of the action of microorganisms, for example, microorganisms selected from the group consisting of bacteria, fungi, e.g., molds, and mixtures thereof. Particularly useful NMDC's include those obtained as a result of the action of *Micrococcus luteus, Aspergillus niger* and mixtures thereof. The contact lens included in the contacting step is preferably disinfected by the action of hydrogen peroxide during or prior to the contacting.

In a further broad aspect of the present invention, methods for disinfecting a contact lens are provided. Such methods comprise contacting a contact lens with a first liquid medium containing a contact lens disinfecting amount of hydrogen peroxide. This contacting occurs at conditions effective to disinfect the contact lens. The disinfected lens is contacted with a second liquid medium containing hydrogen peroxide in the presence of NMDC in an amount effective to promote the destruction of substantially all the hydrogen peroxide in the second liquid medium. In one particularly useful embodiment, the first liquid medium and the second liquid medium are the same liquid medium, preferably an aqueous substantially isotonic liquid medium. In one embodiment, both of the above-noted contacting steps occur at least partially at the same time.

The present invention is further directed to compositions. In one broad aspect, the present invention is directed to compositions which comprise an aqueous substantially isotonic, preferably ophthalmically acceptable, liquid medium containing NMDC. The aqueous substantially isotonic liquid medium preferably includes an effective pH controlling amount of a buffer component.

In another broad aspect of the present invention, compositions comprising a liquid medium containing a contact lens and a contact lens disinfecting amount of hydrogen peroxide are provided. In these compositions, NMDC is provided in an amount effective to promote the destruction of substantially all of the hydrogen peroxide in the liquid medium after being released in tie liquid medium.

In an additional broad aspect of the present invention, compositions are provided which comprise NMDC effective to promote the destruction of hydrogen peroxide; and a barrier component effective to delay the release of the NMDC in a hydrogen peroxide-containing liquid medium, hereinafter referred to as HPLM, for a period of time after the composition is initially contacted with the HPLM. Preferably, the NMDC is present in an amount effective to promote the destruction of substantially all the hydrogen peroxide present in the HPLM in which the composition is released.

DETAILED DESCRIPTION OF THE INVENTION

The present invention is of value where hydrogen peroxide is used to disinfect all types of lenses, e.g., contact lenses, which are benefitted by periodical disinfecting. Such lenses may be made of any suitable material or combination of materials and may have any suitable configuration not substantially deleteriously affected by hydrogen peroxide, the present compositions or the present methods.

The present invention takes advantage of the discovery that non-mammalian-derived catalase (NMDC) provides one or more substantial advantages, for example, enhanced stability, relative to bovine catalase in destroying hydrogen peroxide contact lens disinfectant. NMDC obtained as a result of the action of one or more microorganisms, preferably selected from bacteria, fungi and mixtures thereof, are particularly useful. Excellent results are obtained with NMDC obtained as a result of the action of microorganisms selected from *Micrococcus luteus*, *Aspergillus niger* and mixtures thereof.

In one embodiment, methods for destroying hydrogen peroxide are provided. These methods comprise contacting a contact lens with a liquid medium, preferably an aqueous liquid medium, containing hydrogen peroxide in the presence of NMDC in an amount effective to promote the destruction of substantially all the hydrogen peroxide in the liquid medium, preferably within about 3 hours or about 4 hours of the start of the contacting step.

The present methods preferably involve the contact lens in the liquid medium being disinfected by the action of hydrogen peroxide, for example, during or prior to the contacting.

In another embodiment, methods for disinfecting contact lenses are provided. Such methods comprise contacting a contact lens with a first liquid medium containing a contact lens disinfecting amount of hydrogen peroxide. This contacting occurs at conditions effective to disinfect the contact lens. The disinfected lens is contacted with a second liquid medium, preferably an aqueous liquid medium, containing hydrogen peroxide in the presence of NMDC in an amount effective to promote the destruction of substantially all the hydrogen peroxide in the second liquid medium. Once substantially all the hydrogen peroxide has been destroyed, the disinfected contact lens can be removed from the second liquid medium and placed directly into the eye for safe and comfortable wear. Alternately, the disinfected contact lens can be removed from the second liquid medium, rinsed with saline solution or other suitable liquid medium to remove residual catalase from the lens, and then placed in the eye for safe and comfortable wear. Preferably, the first liquid medium and the second liquid medium are the same, or at least are derived from the same, liquid medium.

In yet another embodiment, compositions comprising an aqueous substantially isotonic liquid medium containing NMDC are provided. Preferably, such aqueous substantially isotonic liquid medium includes an effective pH controlling amount of a buffer component, more preferably effective to control the pH of the liquid medium in the range of about 3 to about 10, for example, about 6 to about 8.

Compositions comprising a liquid medium, for example, as described elsewhere herein, a contact lens and NMDC are also provided. The liquid medium contains a contact lens disinfecting amount of hydrogen peroxide. The NMDC is present in an amount effective to promote the destruction of substantially all the hydrogen peroxide in the liquid medium after being released in the liquid medium.

In a particularly useful embodiment, compositions are provided which result in the delayed release of NMDC. In this embodiment, NMDC in an amount effective to promote the decomposition of hydrogen peroxide is included. A barrier component effective to delay the release of the NMDC in a HPLM for a period of time after the composition is initially contacted with the HPLM is provided. In this embodiment, the NMDC is present in an amount effective to promote the destruction of substantially all of the hydrogen peroxide present in the HPLM in which the composition is released.

Although any number of NMDC catalases may be employed in accordance with the present invention, it is preferred that the NMDC be obtained as the result of the action of one or more microorganisms, more preferably one or more microorganisms selected from bacteria, fungi and mixtures thereof.

The manufacture of such NMDC's may be achieved using conventional and well known processes and techniques. Therefore, a detailed description of such manufacturing processes and techniques is not presented here, and is not considered a part of the present invention.

Excellent results are achieved if the NMDC is obtained as the result of the action of *Micrococcus luteus*, *Aspergillus niger* and mixtures thereof.

The amount of NMDC employed is preferably sufficient to destroy all the hydrogen peroxide present in the HPLM in which the NMDC is released. Excess amounts of NMDC may be employed. However, very large excesses of NMDC, for example, more than about 300% of the amount needed to destroy all the hydrogen peroxide present in the HPLM, are to be avoided since such excessive amounts of NMDC may cause problems with the disinfected lens and/or with the ability to safely and comfortably wear such disinfected lens. NMDC is preferably present in an amount of about 10 to about 1000, more preferably about 20 to about 800, units of catalase activity per milliliter of liquid medium. The amount of NMDC employed depends not only on the amount of hydrogen peroxide to be destroyed, but also on the specific NMDC being used. For example, in an aqueous solution containing about 3% (w/v) hydrogen peroxide, about 100 to about 1000 International Units of catalase activity/ml of solution is preferably used if the catalase is obtained by the action of *Micrococcus luteus*; and about 10 to about 200 International Units of catalase activity/ml of solution is preferably used if the catalase is obtained by the action of *Aspergillus niger*.

In the present invention, hydrogen peroxide is preferably used in a disinfecting amount. A disinfecting amount preferably means such amount as will reduce the microbial burden by one log in three hours. More preferably, the amount of hydrogen peroxide used is such that the microbial load is reduced by one log order in one hour. Particularly preferred are those amounts which reduce the microbial load by one log unit in 10 minutes or less. Aqueous hydrogen peroxide solutions, preferably containing about 0.5% to about 6% of hydrogen peroxide, are known to be effective disinfecting solutions for contact lenses. These solutions are effective at killing bacteria and fungi and other microorganisms which may be found on contact lenses.

The liquid media used are selected to have no substantial detrimental effect on the lens being treated, and on the wearer of the treated lens. The liquid media are constituted to allow, and preferably to even facilitate, the present lens treatment or treatments. The liquid media are preferably aqueous-based and more preferably are aqueous, substantially isotonic liquid media. Particularly useful aqueous liquid media are those derived from saline, e.g., a conventional saline solution or buffered saline solution. During the disinfecting contacting, it is preferred that the aqueous liquid medium have a pH in the range of about 2 or 3 to about 9. During the time in which the residual hydrogen peroxide disinfectant is being destroyed, the pH of the aqueous liquid medium is preferably about 3 or higher, for example, to about 10, or about 6 to about 8.

One important advantage of certain of the NMDC's, for example, catalase obtained by the action of *Aspergillus niger*, is an ability to effectively function in destroying hydrogen peroxide over a broader pH range relative to the effective pH range of bovine catalase. This feature allows the disinfecting to occur under acid conditions, which is often preferred, and the hydrogen peroxide destruction to start at the same acid conditions. Thus, the time required to destroy all the hydrogen peroxide is reduced because it is not necessary to wait until the pH of the liquid medium is adjusted upwardly before contacting the HPLM with the NMDC. By the time the destruction of the hydrogen peroxide is complete, it is preferred that the pH of the liquid medium be in the range of about 6 to about 8.

The liquid media, e.g., aqueous liquid media, employed preferably include a buffer component which is present in an amount effective to maintain the pH of the liquid medium in the desired range. This buffer component may be present in the liquid medium and/or may be introduced into the liquid medium, e.g., either separately or in combination with one or more of the other presently useful components, e.g., with the NMDC. Among the suitable buffer components or buffering agents which may be employed are those which are conventionally used in contact lens care products. Examples of useful buffer components include those with carbonate functionalities, bicarbonate functionalities, phosphate functionalities, borate functionalities, and the like and mixtures thereof. The buffers may be alkali metal and alkaline earth metal salts, in particular sodium and potassium.

In one embodiment, solid compositions, which are preferably initially contacted with the HPLM at substantially the same time as is the lens to be disinfected, can provide for effective lens disinfection and, in addition, effectively destroy the residual hydrogen peroxide remaining in the liquid medium so that the disinfected lens can be removed from the liquid medium and placed into the eye for safe and comfortable wear. Such solid compositions may be present in the form of at least one item, e.g., tablet, capsules, one or more solid particles, granules and the like, which includes a coated portion, e.g., a core such as a core tablet, and a barrier or delayed release component. The coated portion or core includes the NMDC. The barrier component acts to delay the release of the NMDC from the coated portion in the HPLM for a period of time, preferably sufficient to allow the lens to be disinfected. Preferably, the barrier component substantially surrounds or coats the coated portion.

The delayed release of the NMDC into the liquid medium may be accomplished in any one of many suitable ways, a number of which are conventional and well known in the art. For example, the barrier component may be provided by coating a core tablet, pill, granules or other particle or particles or the like, containing the NMDC with a slow dissolving coating material, which may ultimately be completely or only partially soluble in the liquid medium, or by including the NMDC in a matrix from which it may be slowly leached. Also, the matrix may be coated with a slow dissolving material so that the start of the slow release is delayed. The delayed release form of the NMDC is preferably such that substantially no release occurs during a delay period followed by rapid and substantially complete release of the NMDC at the end of the delay period. Such a result may be obtained by coating the NMDC with a slow dissolving coating.

Barrier components suitable as either coatings or as matrices, include water soluble vinyl polymers, such as polyvinylpyrollidone, polyvinylalcohol and polyethyleneglycol; water soluble proteins; polysaccharide and cellulose derivatives, such as methyl cellulose, hydroxypropylmethyl cellulose, sodium carboxymethyl cellulose; alginic acid and its salts and other derivatives; and the like and mixtures thereof.

Although multi-layered (including core and coating layers) tablets or pills are preferred, the delayed release form of the present compositions can be present in any other suitable item or items, such as masses of powders, granules and the like. Delayed release technology is well known in the art as exemplified by the text *Controlled Drug Delivery*, 2nd Ed., Joseph R. Robinson & Vincent H. L. Lee, Eds., Marcel Dekker, Inc., New York, 1987.

The amount of barrier component used is not critical in the present invention provided that such barrier component functions as described herein. The barrier component or components may suitably be present in the range of about 1% or about 5% to about 1000% or more, based on the weight of the NMDC.

The present solid compositions may be produced using any one of many suitable methods, a number of which are conventional and well known in the art. The production method chosen depends, in large measure, on the desired form of the composition. In one particularly useful embodiment, a tableting method, e.g., a conventional tableting method, is employed to produce the present solid compositions in the form of tablets. In tableting a composition according to the invention, conventional tableting additives, such as sugar based excipients, e.g., lactose, surfactants, e.g., sodium lauryl sulphate, polyoxy-ethyleneglycol monoalkyl ethers, alkyl-aryl ethoxylates or saccharide esters, and water soluble polymers, such as polyvinylpyrrolidone and polyethylene glycol, may be employed.

In a particularly useful embodiment, the present compositions further include at least one enzyme effective to remove debris from a contact lens. Among the types of debris that form on contact lens during normal use are protein-based debris, mucin-based debris, lipid-based debris and carbohydrate-based debris. One or more types of debris may be present on a single contact lens.

The enzyme employed may be selected from peroxide-active enzymes which are conventionally employed in the enzymatic cleaning of contact lenses. For example, many of the enzymes disclosed in Huth et al U.S. Reissue Pat. No. 32,672 and Karageozian et al U.S. Pat. No. 3,910,296 are useful in the present invention. These patents are incorporated in their entirety by reference herein. Among the useful enzymes are those selected from proteolytic enzymes, lipases and mixtures thereof. Preferred proteolytic enzymes are those which are substantially free of sulfhydryl groups or disulfide bonds, whose presence may react with the active oxygen in the HPLM to the detriment of the activity of the enzyme. Metallo-proteases, those enzymes which contain a divalent metal ion such as calcium, magnesium or zinc bound to the protein, may also be used.

A more preferred group of proteolytic enzymes are the serine proteases, particularly those derived from Bacillus and Streptomyces bacteria and Aspergillus molds. Within this grouping, the still more preferred enzymes are the derived alkaline proteases generically called subtilisin enzymes. Reference is made to Deayl, L., Moser, P. W. and Wildi. B. S., "Proteases of the Genus Bacillus. II Alkaline Proteases", Biotechnology and Bioengineering, Vol. XII, pp 213–249 (1970) and Keay, L. and Moser, P. W., "Differentiation of Alkaline Proteases form Bacillus Species" Biochemical and Biophysical Research Comm., Vol 34, No. 5, pp 600–604, (1969).

The subtilisin enzymes are broken down into two subclasses, subtilisin A and subtilisin B. In the subtilisin A grouping are enzymes derived from such species are *B. subtilis, B. licheniformis* and *B. pumilis*. Organisms in this sub-class produce little or no neutral protease or amylase. The subtilisin B sub-class is made up of enzymes from such organisms as *B. subtilis, B. subtilis var. amylosacchariticus, B. amyloliquefaciens* and *B. subtilis* NRRL B3411. These organisms produce neutral proteases and amylases on a level about comparable to their alkaline protease production. One or more enzymes from the subtilisin A sub-class are particularly useful.

In addition other preferred enzymes are, for example, pancreatin, trypsin, collaginase, keratinase, carboxylase, aminopeptidase, elastase, and aspergillo-peptidase A and B, pronase E (from *S. griseus*) and dispase (from *Bacillus polymyxa*).

An effective amount of enzyme is to be used in the practice of this invention. Such amount will be that amount which effects removal in a reasonable time (for example overnight) of substantially all of at least one type of debris from a lens due to normal wear. This standard is stated with reference to contact lens wearers with a history of normal pattern of lens debris accretion, not the very small group who may at one time or another have a significantly increased rate of debris accretion such that cleaning is recommended every day, or every two or three days.

The amount of enzyme required to make an effective cleaner will depend on several factors, including the inherent activity of the enzyme, and the extent of its interaction with the hydrogen peroxide present.

As a basic yardstick, the working solution should contain sufficient enzyme to provide about 0.001 to about 3 Anson units of activity, preferably about 0.01 to about 1 Anson units, per single lens treatment. Higher or lower amounts may be used.

Enzyme activity is pH dependent so for any given enzyme, there is a particular pH range in which that enzyme will function best. The determination of such range can readily be done by known techniques.

The present solid compositions which include such lens cleaning enzymes may be structured to release the enzyme in the liquid medium which contacts the composition at any time relative to the other component or components of the composition provided that the released enzyme is effective at the conditions present in the liquid medium to perform the cleaning function, as described herein. In one particularly useful embodiment, the cleaning enzyme is released in the liquid medium prior to or at substantially the same time as NMDC is so released.

Using the present compositions to disinfect, and preferably clean, a contact lens may be accomplished by contacting the lens to be disinfected with the composition, if the composition includes a liquid medium, or with a combination of the composition and a liquid medium at conditions effective to effectively disinfect the lens.

In the event that a debris removing enzyme is present in the composition, the contact lens in the liquid medium is also effectively cleaned of such debris. This cleaning action can occur before the lens is disinfected, at the time the lens is being disinfected, or after the lens is disinfected.

It is preferred that the NMDC not be released into the liquid medium until the lens has been contacted with, e.g., immersed in, liquid medium for a time sufficient, more preferably in the range of about 1 minute to about 4 hours and still more preferably in the range of about 5 minutes to about 1 hour, to effectively disinfect the lens. It is also preferred that substantially all of the residual hydrogen peroxide in the liquid medium be destroyed in less than about 3 hours or about 4 hours, more preferably in less than about 1 hour and still more preferably in less than about 30 minutes, after the NMDC is initially released in the liquid medium.

The disinfecting contacting preferably occurs in a quantity, e.g., about 5 ml to about 15 ml, of an HPLM at a temperature to maintain the liquid medium substantially liquid. It is preferred that the contacting temperature be in the range of about 0° C. to about 100° C., and more preferably in the range of about 10° C. to about 60° C. and still more preferably in the range of about 15° C. to about 30° C. Contacting at or about ambient temperature is very convenient and useful. The contacting preferably occurs for a time to effectively disinfect the lens being treated.

After this disinfecting contacting, the NMDC can be released in the liquid medium to destroy the residual hydrogen peroxide. This "hydrogen peroxide destruction" contacting can occur at the same temperature conditions at which the disinfecting contacting occurred. This contacting occurs for a time sufficient to destroy all the hydrogen peroxide present in the liquid medium. The NMDC may be present in a delayed release form. as described elsewhere herein. Alternately. the disinfected lens can be removed from the HPLM and placed in and contacted with a separate quantity, for example, about 5 ml to about 15 ml, of a liquid medium containing-NMDC to destroy the hydrogen peroxide carried by the disinfected lens. This "separate" contacting can occur at the same temperature conditions at which the disinfecting contacting occurred. This contacting occurs for a time sufficient to destroy all the hydrogen peroxide present in the liquid medium, for example, in less than about 3 hours or about 4 hours, and preferably less than about 1 hour or about 30 minutes.

After such contacting, the liquid medium preferably includes substantially no hydrogen peroxide, and the disinfected lens can be removed from this liquid medium and placed directly into the eye for safe and comfortable wear. Alternately, the disinfected lens can be rinsed, e.g., with saline solution, to free the lens of enzyme or enzymes prior to placing the disinfected lens into the eye.

The following non-limiting examples illustrate certain aspects of the present invention.

EXAMPLES 1 AND 2

A series of samples of NMDC's were tested to determine what effect tableting compression has on the activity of the catalase.

Catalase obtained by the action of *Micrococcus luteus* was selected as the first composition (Example 1). Quantities of this catalase from four (4) separate production lots of this product sold by Solvay Enzymes, Inc. were subjected to conventional compression tableting conditions used to produce catalase tablets from bovine catalase to destroy hydrogen peroxide contact lens disinfectant. This catalase had a molecular weight of 225,000 to 250,000, and a specific activity of more than 65,000 International Units (IU)/mg. This product had a protein purity of more than 97%.

Similarly, catalase obtained by the action of *Aspergillus niger* was selected as the second composition (Example 2). Quantities of this catalase from two (2) separate production lots of this product sold by Genencor Corporation and from two (2) separate production lots of this product sold by Purified Protein, Inc. were subjected to compression tableting as described above. These catalases had a molecular weight of about 323,000, a specific activity of about 7,000 to 12,000 IU/mg, and a protein purity of more than 97%.

Catalase from bovine livers conventionally used to destroy hydrogen peroxide contact lens disinfectant has a molecular weight of about 240,000, a specific activity of more than 65,000 IU/mg and a protein purity of more than 97%.

The theoretical activity of each of the above-noted eight (8) quantities of catalase was calculated. A tablet made from each of these eight quantities of catalase was tested, using conventional procedures, to determine the actual catalase activity of the tablet.

Results of these tests were as follows:

|  | THEORETICAL ACTIVITY | ACTUAL ACTIVITY | LOSS, % |
|---|---|---|---|
| EXAMPLE 1 |  |  |  |
| TABLET A | 7704 | 6880 | 10.7 |
| TABLET B | 5910 | 5118 | 13.4 |
| TABLET C | 5501 | 5533 | 0 |

|  | THEORETICAL ACTIVITY | ACTUAL ACTIVITY | LOSS, % |
|---|---|---|---|
| TABLET D | 7020 | 6450 | 8.1 |
|  |  | AVE. | 8.0 |
| EXAMPLE 2 |  |  |  |
| TABLET A | 875 | 651 | 25.6 |
| TABLET B | 1686 | 1653 | 2.0 |
| TABLET C | 1228 | 1160 | 5.5 |
| TABLET D | 2606 | 2234 | 14.3 |
|  |  | AVE. | 11.8 |

Under similar conditions, catalase obtained from bovine livers lost an average of 24.0% of its theoretical activity.

These results indicate that both *Micrococcus luteus* catalase and *Aspergillus niger* catalase are substantially more stable than catalase obtained from bovine livers when subjected to compression tableting conditions. Such compression tableting conditions are representative of the conditions to which catalase is subjected in making contact lens disinfectant destroying compositions. In effect, these results indicate that such NMDC's can be employed more effectively and efficiently than bovine catalase in a compressed tablet to destroy hydrogen peroxide contact lens disinfectant.

EXAMPLES 3 TO 4

Tablets containing catalase obtained by the action of *Micrococcus luteus* and *Aspergillus niger* and bovine catalase were maintained at 45° C. for a period of time of 90 days. Some of each of these tablets were tested at the beginning of the test, 30 days into the test, 60 days into the test and 90 days into the test to determine catalase activity.

Results of these tests were as follows:

| Raw Material Source | TIME, DAYS | | | |
|---|---|---|---|---|
|  | 0 | 30 | 60 | 90 |
|  | ACTIVITY (% OF INITIAL ACTIVITY) | | | |
| Micrococcus Luteus | 5018 (100%) | 3508 (70%) | 2997 (60%) | 2177 (43%) |
| A. Niger | 2120 (100%) | 1464 (69%) | 1221 (58%) | 729 (34%) |
| Bovine Liver | 5319 (100%) | 2242 (42%) | 634 (12%) | 404 (7.6%) |

These tests indicate that the stability of the NMDC's is substantially greater than the stability of bovine catalase. Thus, the catalase obtained by the action of *Micrococcus luteus* and *Aspergillus niger* have increased effective shelf lives, thus making these materials very useful for consumer products, such as for contact lens-related products.

EXAMPLE 5

Quantities of aqueous liquid compositions containing catalase obtained by the action of *Micrococcus luteus* and bovine catalase were held at 45° C. for a period of time of 90 days. Samples of each of these materials were taken at the beginning of the test, 30 days into the test, 60 days into the test and 90 days into the test to determine catalase activity.

Results of these tests were as follows:

| Raw Material Source | TIME, DAYS | | | |
|---|---|---|---|---|
| | 0 | 30 | 60 | 90 |
| | ACTIVITY (% OF INITIAL ACTIVITY) | | | |
| Micrococcus Luteus | 244 (100%) | 265 (109%) | 261 (107%) | 253 (104%) |
| Bovine Liver | 500 (100%) | 325 (65%) | 306 (61%) | 176 (35%) |

These results demonstrate that the NMDC has enhanced stability in a liquid medium relative to bovine catalase. Certain of the products used in contact lens care involve catalase present in a liquid medium. These results indicate that such liquid products containing NMDC have increased effective shelf lives relative to similar liquid products with bovine catalase.

The above examples make clear that the presently useful NMDC's are more stable than the conventionally used bovine catalase in contact lens treating service.

EXAMPLE 6

A layered tablet, having a core tablet surrounded by a delayed release layer. is prepared. The layered tablet has the following composition:

| CORE TABLET | |
|---|---|
| Sodium Chloride | 89.4 mg |
| Dibasic Sodium Phosphate (Anhydrous) | 12.5 mg |
| Monobasic Sodium Phosphate Monohydrate (Anhydrous) | 0.87 mg |
| Polyethylene Glycol (Molecular Weight of about 3350) | 1.05 mg |
| Lyophilized Catalase Derived from *Micrococcus luteus* | 7020 International Units |
| COATING LAYER | |
| Hydroxypropylmethyl-cellulose | 8 mg |

This layered tablet is used to disinfect a conventional soft contact lens as follows:

10 ml of a 3% (w/v) aqueous solution of hydrogen peroxide is provided at room temperature. The contact lens to be disinfected and the layered tablet are placed in the solution at the same time. For approximately 45 minutes. the solution remains substantially quiet. i.e.. substantially no bubbling (gas evolution) takes place. For the next approximately 2 hours, the solution bubbles. After this period of time, the solution becomes and remains quiet. 3 hours after the contact lens is first introduced into the solution. it is removed from the solution, rinsed free of catalase with a saline solution and placed into the wearer's eye. It is found that the contact lens is effectively disinfected. Also, the lens wearer experiences no discomfort or eye irritation from wearing the disinfected contact lens. The bubbling of the solution provides an indication that hydrogen peroxide destruction is occurring. An indication that the peroxide destruction is complete is provided when the bubbling stops.

EXAMPLE 7

A layered tablet is prepared as in Example 6 except that sufficient subtilisin A is included as an outer layer to provide the tablet with 10 ppm (by weight) of this enzyme.

This cleaning enzyme containing tablet is used to disinfect and clean a protein-based debris laden soft contact lens. 10 ml of a 3% (w/v) aqueous solution of hydrogen peroxide is provided at room temperature. The contact lens to be disinfected and cleaned and the cleaning enzyme-containing layered tablet are placed in the solution at the same time. For approximately 45 minutes the solution remains substantially quiet. For the next approximately 2 hours, the solution bubbles. After this period of time, the solution becomes and remains quiet. 10 hours after the contact lens is first introduced into the solution, it is removed from the solution, rinsed free of enzyme with a saline solution, and placed into the wearer's eye. It is found that the contact lens is effectively disinfected and cleaned of protein-based debris. The lens wearer experiences no discomfort or eye irritation from wearing the disinfected and cleaned contact lens.

EXAMPLE 8

A layered tablet, having a core tablet surrounded by a delayed release layer, is prepared. The layered tablet has the following composition:

| CORE TABLET | |
|---|---|
| Sodium Chloride | 89.4 mg |
| Dibasic Sodium Phosphate (Anhydrous) | 12.5 mg |
| Monobasic Sodium Phosphate Monohydrate (Anhydrous) | 0.87 mg |
| Polyethylene Glycol (Molecular Weight of about 3350) | 1.05 mg |
| Lyophilized Catalase Derived from *Aspergillus niger* | 500 International Units |
| COATING LAYER | |
| Hydroxypropylmethyl cellulose | 8 mg |

This layered tablet is used to disinfect a conventional soft contact lens as follows:

10 ml of a 3% (weight/volume) aqueous solution of hydrogen peroxide is provided at room temperature. The contact lens to be disinfected and the layered tablet are placed in the solution at the same time. For approximately 45 minutes, the solution remains substantially quiet. For the next approximately 2 hours, the solution bubbles. After this period of time, the solution becomes and remains quiet. 3 hours after the contact lens is first introduced into the solution, it is removed from the solution, rinsed free of catalase with saline solution, and placed into the wearer's eye. It is found that the contact lens is effectively disinfected. Also, the lens wearer experiences no discomfort or eye irritation from wearing the disinfected contact lens.

EXAMPLE 9

A layered tablet is prepared as in Example 8 except that sufficient subtilisin A is included as an outer layer to provide the tablet with 10 ppm (by weight) of this enzyme.

This cleaning enzyme containing tablet is used to disinfect and clean a protein-based debris laden soft contact lens.

10 ml of a 3% (w/v) aqueous solution of hydrogen peroxide is provided at room temperature. The contact lens to be disinfected and cleaned and the cleaning enzyme-containing layered tablet are placed in the solution at the same time. For approximately 45 minutes the solution remains substantially quiet. For the next approximately 2 hours, the solution bubbles. After this period of time, the solution becomes and remains quiet. 10 hours after the contact lens is first introduced into the solution, it is removed from the solution, rinsed free of enzyme with a saline solution, and placed directly into the wearer's eye. It is found that the contact lens is effectively disinfected and cleaned of protein-based debris. The lens wearer experiences no discomfort or eye irritation from wearing the disinfected and cleaned contact lens.

EXAMPLE 10

Two unit dose (10 ml) formulations are prepared and have the following compositions:

|  | Composition 10A | Composition 10B |
|---|---|---|
| Sodium chloride | 0.85% | 0.85% |
| Dibasic sodium phosphate heptahydrate | 0.402% | 0.402% |
| Monobasic sodium phosphate monohydrate | 0.091% | 0.091% |
| Disodium Edetate | 0.100% | 0.100% |
| Liquid Catalase[1] | 260 International Units/ml (obtained by the action of *Micrococcus luteus*) | 60 International Units/ml (obtained by the action of *Aspergillus niger*) |
| Purified Water | QS-ad | QS-ad |

[1] Each of these liquid catalases include 35–45% (weight) glycerol and 10% (weight) ethanol.

Each of these compositions were used to destroy residual amounts of hydrogen peroxide contact lens disinfectant as follows:

10 ml of 3% w/v aqueous solution of hydrogen peroxide is provided at room temperature. A contact lens to be disinfected is placed in the solution for approximately twenty (20) minutes. Afterward, the disinfected contact lens is removed from the hydrogen peroxide solution and placed in 10 ml of either composition 10A or composition 10B. After about ten (10) minutes, the disinfected contact lens is removed from the solution, rinsed in saline solution and placed into the wearer's eye. The lens wearer experiences no discomfort or eye irritation from wearing disinfected contact lens.

EXAMPLE 11

Multi dose (100 ml) quantities of the following compositions are prepared and have the following compositions:

|  | Example 11A | Example 11B |
|---|---|---|
| Sodium Chloride | 0.60% | 0.60% |
| Sodium Borate Decahydrate | 0.32% | 0.32% |
| Boric Acid | 0.21% | 0.21% |
| Sorbic Acid | 0.10% | 0.10% |
| Disodium Edetate | 0.20% | 0.20% |
| Liquid Catalase[1] | 260 units/ml (obtained by the action of *Micrococcus luteus*) | 60 units/m (obtained by the action of *Aspergillus niger*) |
| Purified Water | QS-ad | QS-ad |

[1] Each of these liquid catalases include 35–45% (weight) glycerol and 10% (weight) ethanol.

A quantity, 10 ml, of each of these compositions was used to destroy residual hydrogen peroxide contact lens disinfectant in a manner substantially similar to that described in Example 10. After the disinfected contact lens is removed from each of these compositions, rinsed with saline solution and placed into the wearer's eye, the lens wearer experiences no discomfort or eye irritation from wearing the disinfected contact lens.

While this invention has been described with respect to various specific examples and embodiments, it is to be understood that the invention is not limited thereto and that it can be variously practiced within the scope of the following claims.

What is claimed is:

1. A composition comprising:
   non-mammalian-derived catalase obtained as a result of the action of *Aspergillus niger* and being effective to promote the destruction of hydrogen peroxide in a hydrogen peroxide-containing liquid medium; and
   a barrier component effective to delay the release of said non-mammalian-derived catalase in the hydrogen peroxide-containing liquid medium for a period of time after said composition is initially contacted with the hydrogen peroxide-containing liquid medium, said barrier component including a material selected from the group consisting of cellulose derivatives and mixtures thereof.

2. The composition of claim 1 wherein said barrier component includes hydroxypropylmethyl cellulose.

3. The composition of claim 2 wherein said barrier component is water soluble.

4. The composition of claim 1 wherein said non-mammalian derived catalase is present in an amount in the range of about 10 to about 200 International Units of catalase activity per milliliter of the hydrogen peroxide-containing medium.

5. The composition of claim 1 wherein said barrier component is water soluble.

6. A method for disinfecting a contact lens which comprises:
   contacting a contact lens with a hydrogen peroxide-containing liquid medium at conditions effective to disinfect said contact lens; and
   contacting said hydrogen peroxide-containing liquid medium in the presence of said contact lens with a composition comprising non-mammalian catalase obtained as a result of the action of *Aspergillus niger* and being effective to promote the destruction of hydrogen peroxide in a hydrogen peroxide-containing liquid medium; and a barrier component effective to delay the release of said non-mammalian-derived catalase in the hydrogen peroxide-containing liquid medium for a period of time after said composition is initially contacted with the hydrogen peroxide-containing liquid medium, said barrier component including a material selected from the group consisting of cellulose derivatives and mixtures thereof.

7. The method of claim 6 wherein said barrier component includes hydroxypropylmethyl cellulose.

8. The method of claim 7 wherein said hydrogen peroxide-containing liquid medium is an aqueous liquid medium.

9. The method of claim 7 wherein said non-mammalian derived catalase is present in an amount in the range of about 10 to about 200 International Units of catalase activity per milliliter of the hydrogen peroxide-containing medium.

10. The method of claim 9 wherein said hydrogen peroxide-containing liquid medium is an aqueous liquid medium.

11. The method of claim 6 wherein said non-mammalian derived catalase is present in an amount in the range of about 10 to about 200 International Units of catalase activity per milliliter of the hydrogen peroxide-containing medium.

12. The method of claim 6 wherein said hydrogen peroxide-containing liquid medium is an aqueous liquid medium.

13. A composition comprising:

non-mammalian-derived catalase obtained as a result of the action of *Aspergillus niger* and being effective to promote the decomposition of hydrogen peroxide in a hydrogen peroxide-containing liquid medium, said non-mammalian derived catalase is present in an amount in the range of about 10 to about 200 International Units of catalase activity per milliliter of the hydrogen peroxide-containing medium; and a barrier component effective to delay the release of said non-mammalian-derived catalase in the hydrogen peroxide-containing liquid medium for a period of time after said composition is initially contacted with the hydrogen peroxide-containing liquid medium, said barrier component including hydroxypropylmethyl cellulose.

14. The composition of claim 13 wherein said barrier component is water soluble.

* * * * *

UNITED STATES PATENT AND TRADEMARK OFFICE
CERTIFICATE OF CORRECTION

PATENT NO.    : 5,766,931
DATED         : June 16, 1998
INVENTOR(S)   : Cook et al.

It is certified that error appears in the above-identified patent and that said Letters Patent is hereby corrected as shown below:

Column 23,
Line 23, "tie" should be -- the --.

Column 5,
Line 4, "units" should be -- International Units --.

Column 9,
Line 6, "containing-NMDC" should be -- containing NMDC --.

Column 16,
Line 4, "decomposition" should be -- destruction --.

Signed and Sealed this

Third Day of June, 2003

JAMES E. ROGAN
*Director of the United States Patent and Trademark Office*